United States Patent [19]

Cox

[11] Patent Number: 4,776,612
[45] Date of Patent: Oct. 11, 1988

[54] DEVICES FOR RECORDING TEST RESULTS, AND TEST KITS COMPRISING THEM

[75] Inventor: Philip Cox, London, England

[73] Assignee: Unilever Patent Holding B.V., Rotterdam, Netherlands

[21] Appl. No.: 33,364

[22] Filed: Apr. 2, 1987

[30] Foreign Application Priority Data

Apr. 3, 1986 [GB] United Kingdom ............... 8608157

[51] Int. Cl.⁴ .................................... B42D 15/00
[52] U.S. Cl. ................... 283/1 A; 283/48 R
[58] Field of Search ............. 116/200, 201; 283/1 A, 283/48 R; 356/243, 244; 422/58; 435/10, 11; 436/95

[56] References Cited

U.S. PATENT DOCUMENTS

| | | | |
|---|---|---|---|
| 1,979,283 | 11/1934 | Osborn | 283/48 R |
| 3,964,871 | 6/1976 | Hochstrosser | 435/10 |
| 4,174,178 | 11/1979 | Ouchi et al. | 356/244 X |
| 4,270,772 | 6/1981 | Bodily | 283/1 A |
| 4,523,852 | 6/1985 | Bauer | 356/243 X |
| 4,568,184 | 2/1986 | Krantz et al. | 422/58 X |

FOREIGN PATENT DOCUMENTS

0164180 12/1985 European Pat. Off. .
224667 7/1985 Fed. Rep. of Germany .
224409 7/1985 Fed. Rep. of Germany .

*Primary Examiner*—Paul A. Bell
*Attorney, Agent, or Firm*—Cushman, Darby & Cushman

[57] ABSTRACT

A recording device for recording results of a series of chemical tests, each of said tests being adapted to produce a change of color or other visual texture of a test material, said recording device comprising:

(a) a recording surface which is capable of being marked by a user of said test,
(b) an array of recording zones on said recording surface, said zones comprising, for each of a respective series of occasions on which an example of said test is to be performed, a series of zones each to be associated with a respective possible outcome of said test on said occasion; and
(c) said device also carrying, for each said zone, a representation of a color or other visual texture of said test material corresponding to said respective possible outcome of said test.

6 Claims, 2 Drawing Sheets

DEVICES FOR RECORDING TEST RESULTS, AND TEST KITS COMPRISING THEM

This invention relates to a device for recording test results, especially results of chemical tests which are visible, and to test kits comprising such devices, and to methods of testing by the use of such test kits and recording devices. The invention concerns arrangements which are intended to enable especially unskilled users to make systematic measurements and records of test results and draw useful conclusions from them.

A number of available chemical tests, especially clinical chemical tests, give results which are visible by a change of colour or turbidity or other visual character, which may be qualitative or semi-quantitative.

The prior art comprises a number of colour comparator devices for deriving a quantitative test result from a coloured test material, to a reasonable degree of precision having regard to this method of handling without precision measuring electronics.

A prior art search related to the subject of this invention has revealed the following:

DD No. 224 667 (Akad. Wissenschaft DDR) describes a colour comparator for use in evaluating analytical elements such as chemical test strips and the like, on the principle of stepped colour scales. However, this device is apparently intended for laboratory use, to handle reflectance and transmission observations and to use a number of exchangeable stepped scales. No special techniques are suggested for recording test results.

DD No. 224 409 (Friedrich-Schiller-Universität) describes a system for an operator who has to evaluate large numbers of screening, immunological, or enzymatic tests or the liketo evaluate and document the results safely and rationally. The system is shown as comprising a clear pvc documentation sheet marked with gridlines and placed over a multiwell tray containing test reaction mixes showing fluorescence according to the result of the individual test. The arrangement is such that a cell of the grid on the sheet overlies each well, and the sheet can be marked with a marking appropriate to the contents of the well as seen through the sheet. Various arrangements for holding standard fluorescent reference materials near to the location of doubtful cells are described, as well as a method of providing positive control or calibration wells in the multiwell test tray.

U.S. Pat. No. 3,964,871 (Becton Dickinson) describes a disposable indicator which comprises an indicator strip for measuring biological substances such as glucose in biological fluids. The indicator strip has plural indicating reagents for the analyte, each located at a separate zone of a support member and at least two of said reagents indicate the presence of different concentrations of glucose in solution. The aim is to provide test reagent devices which are easy to read, and give clearly distinguishable areas of reacted indicator reagent according to the amount of analyte in the sample which has been tested.

U.S. Pat. No. 4,568,184 (Mast Immunosystems) describes a reader card for mounting an exposed strip sample of photographic film which is to be measured in a densitometer. The card has space on it for writing various indicia and information relevant to the sample.

It has been found desirable by the present inventors to devise a method by which the results of visual comparison of test samples with reference materials can be converted to a handy form for purposes of charting and interpretation by persons who are not skilled in the practice of recording laboratory experiments and presenting results in graphical form.

According to the present invention, we provide a recording device for recording results of series of a chemical tests, each of said tests being adapted to produce a change of colour or other visual texture of a test material, e.g. a test reagent material, the device comprising:

(a) a recording surface which is capable of being marked by a user of said test;
(b) an array of recording zones on said recording surface, said zones comprising, for each of a series of respective occasions on which an example of said test is to be performed, a series of zones each to be associated with a respective possible outcome of said test on said occasion; and
(c) said device also carrying, for each said zone, a representation or likeness of a colour or other visual texture of said test material corresponding to said respective possible outcome of said test.

Said representation will normally be located as close as possible to said corresponding recording zone, preferably at or in or adjacent to said zone. Thus, in many cases, the representation of the colour or other visual texture corresponding to the possible outcome of each test is present on the recording surface as a zone actually made in that colour or visual texture, so that the colour of the recording surface of the zone constitutes the representation. In a preferred example described below, each recording zone is actually made in the colour or visual texture of the test outcome to be recorded by marking in that zone. Alternatively, the associated representation may be conveniently carried directly adjacent to the corresponding recording zone.

Where the outcome of the test is a coloured material, the representation or likeness may be most conveniently an ordinary printed colour or transparency of corresponding intensity and hue.

In a preferred example, said array of zones comprises a two-dimensional array comprising columns of zones, each said column corresponding to a plural number of said possible outcomes of said test, and wherein said columns are arranged side by side to show rows of recording zones of similar colour. Also in a preferred example, said rows of recording zones are made with successively deeper colour in successive higher rows.

Where the outcome of the test is represented by a change of turbidity, the representation may be a transparency of a corresponding colour or degree of capacity, or it may be a printed representation of an object such as a printed character as seen through a turbid medium of corresponding turbidity, or any other representation of the appropriate degree of turbidity.

The recording zones may conveniently be arranged as a two-dimensional array. The array need not be marked with numbers but it will in general carry indicia to distinguish the series of zones reserved for the recording of each of a series of tests, for example indicia distinguishing each column of zones from neighbouring columns of zones. Such indicia may indicate for example, hour of the day or day of the week or month, or sample number.

Also provided by the invention is a test kit comprising a recording device as described above, together with at least one test device but preferably and in most cases a plurality of test devices, said at least one test device adapted to show a test result corresponding to the range of colours or other visual textures displayed as representations on the recording device. Generally each test device carries at least one chemical reagent adapted to react with a sample, especially a biological liquid sample such as for example a blood or urine sample.

The test device can be in any shape or form and can be one that is adapted for example to perform any of the many known chromogenic test reactions familiar in clinical chemistry: it may be for example a solid strip or body which is adapted to develop a colour or change of light absorbency on its surface as a result of a test procedure, corresponding to the likeness or representations figuring on the recording device. (See for example a suitable example of such a device and test as shown and described in European Specification No. 0 164 180). Alternatively a suitable test device can comprise a liquid-containing cell which develops a colour or change of light absorbency in the liquid contained therein as a result of the test.

Alternatively the test device may be for example a transparent tube or other vessel in which a liquid-phase reaction takes place—e.g. one of the known reactions, e.g. agglutination reactions, or other reaction of the kind that can be monitored by turbidimetry or nephelometry. In such a case, the tube or other vessel can carry a visible object to be seen by the user through the reaction liquid with a degree of haziness corresponding to the result of the test reaction.

The invention also provides corresponding uses and methods of testing, in which said recording devices and test kits are used as described herein.

The invention is illustrated by reference to the accompanying drawings, FIGS. 1–4.

Figure 1:
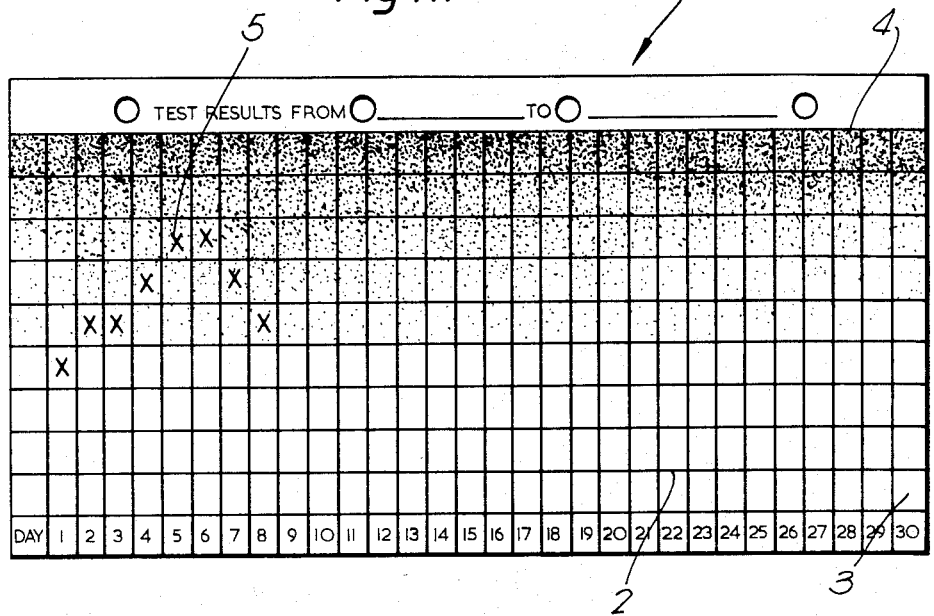
FIG. 1 shows a first embodiment of a test device according to the invention in the form of a recording chart with coloured zones.

Referring to FIG. 1 of the drawings, a test chart carries a two-dimensional grid of rectangles 2 which delineate recording zones carrying row-wise printed (e.g. blue) coloured shading.

Lowermost row marked 3 is plain white or faintly coloured and increasing shades of blue are carried by successive rows up to the top row marked 4.

Below the bottom row there are markings to indicate that each vertical row represents a test for one day. The vertical bars between rows can be made heavier than the horizontal bars between levels in order to emphasise this. The top of the chart has spaces for carrying general identifying indicia, e.g. names and/or dates.

The shades of colouring in each of the rows from bottom row 3 to top row 4 are chosen and adjusted to provide representations of the colour to be obtained by the use of a corresponding test device, of which an example is shown diagrammatically in FIGS. 2(a) and (b). In FIG. 1, there are diagrammatically illustrated nine rows of recording zones, of graded absorbency or hue, increasing in intensity from bottom to top. In alternative and presently preferred arrangements a lesser number, e.g. five rows and grades, may be sufficient.

The test device of FIGS. 2(a) and (b) comprises a handle 21 and a sensitised end 22, essentially as in European specification No. 0 164 180 (Unilever). The sensitised end develops a (e.g. blue) colour to the extent of a test result obtained in any of the known suitable ways of arranging and carrying out clinical strip or peg tests, according to a set of instructions supplied to the user.

The instructions to the user include directions for plotting the test results as one of a sequence of test results on the recording device of FIG. 1. The user is instructed to hold the coloured test device end alongside the column in the chart corresponding to the day of the test, and to move the test device up or down the column until a colour match is found, and finally to make a mark in the column next to the device in its matching position.

When this series of operations has been carried out on a series of tests, the effect is that the chart carries a graph of test results made up of the markings put down by the user, and useful interpretation may be based for example on a peak in the graph or a slope in the sequence of test-result markings.

This form of charting can be especially useful in connection with a series of immunotests made specific by means of appropriate antibodies for human luteinising hormone (LH): such a series of tests may for example be carried out on female urine to assess the point of ovulation during the course of the menstrual cycle, for the purpose of identifying the fertile period of the mestrual cycle of the subject of the test.

Figure 2:
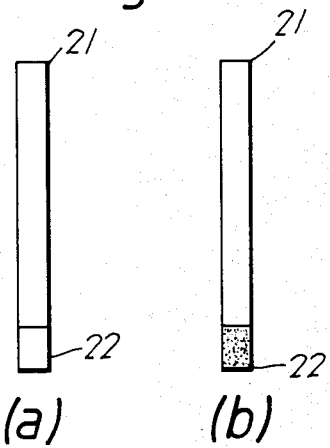
FIG. 2 shows a test strip to be used with the chart of FIG. 1.

For example, a useful series of instructions to enable an unskilled user to use the embodiment of FIGS. 1–2 in the form of a test for human luteinising hormone during the menstrual cycle to construct a record to enable easy assessment of the point of ovulation is as follows:

(a) Begin testing on the tenth day after the beginning of the subject's last menstrual period:

(b) Carry out each day's test with a fresh test stick according to the detailed instructions for using the stick:

(c) When you have finished the test hold the test stick with its tip against the record chart immediately above the figure showing the day of the month:

(d) Move the tip straight up the column until you find the square that most closely matches the colour of the tip on the stick:

(e) Mark this matching square clearly with a cross:

(f) Repeat steps (a) to (e) every day until you see a definite colour increase of at least two squares above the previous days' levels:

(g) This increase indicates that ovulation will most likely occur within a day and a half of the definite increase.

Figures 3, 4:
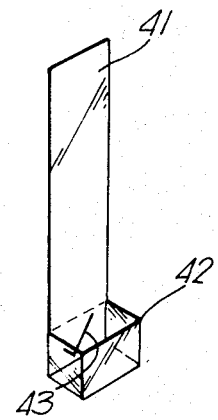
FIG. 3 shows a second embodiment of a test device according to the invention in the form of a recording chart with zones carrying representations of a test object seen through liquids with varying turbidity.
FIG. 4 shows a test tube device to be used with the chart of FIG. 3.

FIGS. 3 and 4 illustrate diagrammatically a recording chart and associated test device according to a further embodiment of the invention. The recording chart 31 of FIG. 3 is arranged in columns as is the chart of FIG. 1. Only two out of several columns are shown in FIG. 3. In FIG. 3, each column has a series of representations, of which only the two most extreme representations 32 and 33 are shown in FIG. 3: each representation shows a part 43 of the test device of FIG. 4 as seen through liquids of varying turbidity, with clear representations in row 32, and very cloudy representations in row 33, and intermediately cloudy representations (not shown) in the intermediate rows between row 32 and row 33.

Adjacent to each representation is a recording zone such as zone 34. Other features of the test recording chart are analogous to FIG. 1.

FIG. 4 shows an associated test device having a handle 41, a liquid-receiving chamber 42 with a transparent wall or wall zone, and a test object or character 43 so placed that it can be seen through the liquid when contained in chamber 42.

Chamber 42 can be used for known immunotests resulting in changes of turbidity or cloudiness, and the results can be compared with the multiple columns of representations on the recording device of FIG. 3, in a similar manner to the use described above for FIG. 1.

The invention extends to many modifications and variations and includes in particular all combinations and subcombinations of features disclosed herein, as will be apparent to those skilled in the art.

I claim:

1. A recording device for recording results of a series of chemical tests, each said test being adapted to produce a change of color or other visual appearance of a test material, said device comprising:
    (a) a recording surface which is capable of being marked by a user of said test;
    (b) an array of recording zones on said recording surface, one recording zone for each of a series of occasions on which a said test is to be performed, and each said recording zone including a series of outcome zones each associated with a possible outcome of said test on a said occasion, whereby a two-dimensional array of outcome zones is provided on said recording surface;
    (c) for each recording zone, at or adjacent said outcome zones, a series of representations of colors or other visual appearances of said test material corresponding to each of the possible outcomes of which one is to be recorded in each said recording zone;
    whereby, in use, when markings are made by a user on a said recording device, one marking for each of a series of tests carried out by the user, and one marking per recording zone at or adjacent the outcome zone associated with that representation of the test outcome which corresponds to the appearance of the test result obtained for recording, said markings yield a graph of the test results made up of said markings.

2. A device according to claim 1, wherein each said representation is constituted by a corresponding colour of said recording surface in each corresponding zone.

3. A device according to claim 2, wherein said array of zones comprises a two-dimensional array comprising columns of zones, each said column corresponding to a plural number of said possible outcomes of said test, and wherein said columns are arranged side by side to show rows of recording zones of similar colour.

4. A device according to claim 3, wherein said rows of recording zones are made with successively deeper colour in successive higher rows.

5. A device according to claim 4, wherein each column is associated with distinctive indicia.

6. The combination of a recording device according to claim 1, 2, 3, 4 or 5 with at least one test device adapted to provide test results showing colour or other visual appearance as represented in said recording device.

* * * * *

UNITED STATES PATENT AND TRADEMARK OFFICE
CERTIFICATE OF CORRECTION

PATENT NO. : 4,776,612

DATED : October 11, 1988

INVENTOR(S) : Cox

It is certified that error appears in the above-identified patent and that said Letters Patent is hereby corrected as shown below:   Title page:

Item [73], correct to read:

--[73] Assignee: Unilever Patent Holdings B.V.
Rotterdam, The Netherlands --

Signed and Sealed this

Thirteenth Day of June, 1989

Attest:

DONALD J. QUIGG

*Attesting Officer*     *Commissioner of Patents and Trademarks*